United States Patent [19]
Sickles et al.

[11] Patent Number: 6,147,254
[45] Date of Patent: Nov. 14, 2000

[54] PROCESS FOR RESOLVING MIXTURES OF CARBOCYCLIC STEREOISOMERS

[75] Inventors: Barry Riddle Sickles; Kenneth James Ingold, both of Durham, N.C.; Christopher John Wallis, Stevenage, United Kingdom

[73] Assignee: Glaxo Wellcome Inc., Research Triangle Park, N.C.

[21] Appl. No.: 09/319,496

[22] PCT Filed: Dec. 4, 1997

[86] PCT No.: PCT/EP97/06782

§ 371 Date: Aug. 6, 1999

§ 102(e) Date: Aug. 6, 1999

[87] PCT Pub. No.: WO98/24741

PCT Pub. Date: Jun. 11, 1998

[30] Foreign Application Priority Data

Dec. 7, 1996 [GB] United Kingdom .................... 9625455

[51] Int. Cl.$^7$ ................................................. C07B 57/00
[52] U.S. Cl. ....................... 562/402; 562/401; 560/115; 560/121
[58] Field of Search .................. 560/115, 121; 562/401, 402

[56] References Cited

FOREIGN PATENT DOCUMENTS

| | | | |
|---|---|---|---|
| 424064A1 | 4/1991 | European Pat. Off. | ...... C07C 233/52 |
| 0 590 685 | 4/1994 | European Pat. Off. | . |
| 590685A1 | 4/1994 | European Pat. Off. | ...... C07C 231/20 |

OTHER PUBLICATIONS

Allan, R.D. et al., Synthesis of Analogues of GABA. XV Preparation and Resolution of Some Potent Cyclopentene and Cyclopentane Derivatives, *Aust. J. Chem.*, 1986, 39: 855–864.

Kam, B.L. et al., Carbocyclic Sugar Amines: Synthesis and Stereochemistry of Racemic α– and β–Carbocyclic Ribofuranosylamine, Carbocyclic Lyxofuranosylamine, and Related Compounds, *J. Org. Chem.*, 1981, 46, 3268–3272.

Csuk, Rene et, "Biocatalytical transformations, IV. Enantioselective enzymic hydrolyses of building blocks for the synthesis of carbocyclic nucleosides", Tetrahedron: Asmmetry, 1994, 5(2), 269–76, 1994.

Daluge, Susan et al: "Synthesis of Carbocylic Aminonucleosides" J. Org. Chem. (1978), 43(12), 2311–20, 1978.

Taylor S J C et al: "Development of the Biocatalytic Resolution of 2–Azabicyclo 2.2.1Hept–5–En–3–One as an Entry to Single–Enantiomercarbocyclic Nucleosides" Tetrahedron: Asymmetry, vol. 4, No. 6, pp. 1117–1128, 1993.

Allan R D et al: Synthesis of Analogues of Gaba. XV. Preparation and Resolution of Some Potent Cyclopentene and Cyclopentane Derivatives Australian Journal of Chemistry, vol. 39, No. 6, pp. 855–864, 1986.

Taylor S J C et al.: "Chemoenzymatic Synthesis of (–)–carbovir using a whole cell catalyse resolution of 2 azabicyclo [2.2.1] hept–5–en–3–one" Journal of the Chemical Society, Chemical Communications., Letchworth GB, pp. 1120–1121, 1990.

M Konishi et al.: "Cispentacin, a new antifungal antibiotic" Journal of Antibiotics., vol. XLII, No. 12, Tokyo JP, pp. 1749–1755, 1989.

Toyota, Akemi et al: "Synthesis of nucleotides and related compounds. Addition of molecular fluorine to bicyclo[2.2.1] hept–2–ene derivatives and conversion to fluorine–containing carbocylic nucleotides" Tetrahedron Lett. (1994), 35(31), 5665–8 1994.

Grenn and Wuts, Protective Groups in Organic Chemistry, 2nd ed., John Wiley & Sons, Inc., NY 1991.

*Primary Examiner*—Johann Richter
*Assistant Examiner*—Brian J. Davis
*Attorney, Agent, or Firm*—Karen L. Prus

[57] ABSTRACT

A process for the preparation of carbocyclic stereoisomers of formulae (I), (I'), (IIA'), (IIB'), (VA') and (VB'), including enantiomerically pure (IIA'), (I) and (I') utilizing fractional crystallization of salts formed with a chiral base; a reducing agent; a protecting group removing agent or a protecting group providing agent.

5 Claims, No Drawings

PROCESS FOR RESOLVING MIXTURES OF CARBOCYCLIC STEREOISOMERS

This application is filed pursuant to 35 U.S.C. 0 371 as a United States National Phase Application of International Application No. PCT/EP97/06782 filed Dec. 4, 1997, which claims priority from 9625455.2 filed Dec. 7, 1996.

The present invention relates to processes for the preparation of compounds of formula (I) or of formula (I'), substantially free of the corresponding enantiomer, involving resolving an enantiomeric mixture of a compound of formula (IIA') and a compound of formula (IIB') by formation of a salt with an optically pure base and fractional crystallisation.

Enantiomerically pure compounds of formula (I) and (I')

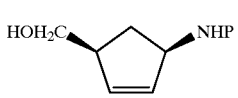

(I) wherein P is H,
(I') wherein P is a protecting group;
are used as intermediates in the manufacture of (−)-(1S, 4R)-4-[2-amino- 6-(cyclopropylamino)-9H-purin-9-yl]-2-cyclopentene-1-methanol (1592U89), a compound currently undergoing clinical investigation as an anti-Human Immunodeficiency Virus (HIV) drug.

The compound 1592U89 is described in EP 0434450 and has the following structure:

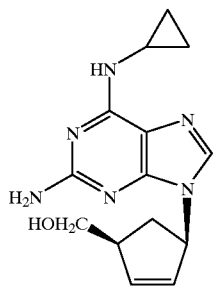

There exists, at the present time, the need to synthesise large quantities of 1592U89 for clinical trials. In the future, once 1592U89 has been approved by the national medicines regulatory agencies, for example the Food and Drug Administration in the U.S., large quantities of 1592U89 will be required for sale as a prescription medicine for the treatment of HIV infections.

Such processes for the manufacture of 1592U89 using enantiomerically pure compounds of formula (I) are described generally in GB patent application No. 9607052.9 and PCT Application No. WO91/15490.

An alternative to such synthetic routes would be to synthesise 1592U89 using enantiomerically mixed intermediates and then resolve the final product, such as described in Example 7 of EP 0434450. However, such a route is not economically viable since purification techniques are not sufficiently efficient to resolve the mixture on such a large scale and would lead to wastage of the final product not in the desired enantiomeric form.

At present there exist two commercially viable routes for the synthesis of enantiomerically pure compounds of formula (I).

A)

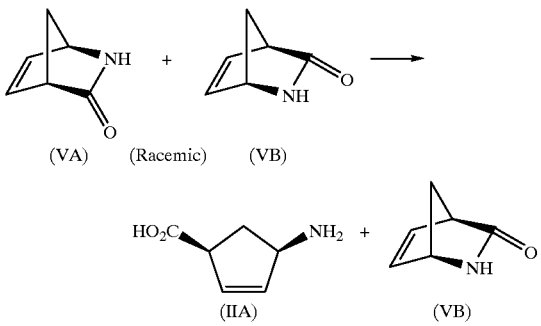

B)

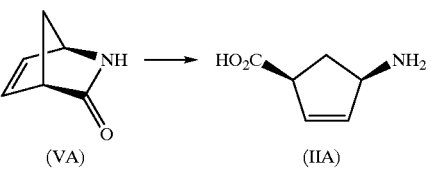

Route A) is an enantioselective hydrolysis of the racemic lactam (VA and VB) using selective enzymes (lactamases) to produce the desired enantiomerically pure/enriched aminocyclopentene carboxylic acid (IIA), such processes are described in European Patent No. 0424064.

Route B) is a non-selective hydrolysis of enantiomerically pure/enriched lactam to produce the desired enantiomerically pure/enriched aminocyclopentene carboxylic acid (IIA). Processes for producing enantiomerically pure/enriched lactam are described in European Patent No. 0424064 and Taylor et al, J. Chem. Soc. Chem. Comm. (1990) 112b.

The compound of formula (IIA) may be converted to the compound of formula (I) by reduction with reagents capable of converting carboxylic acids to alcohols, for example lithium aluminium hydride or borane.

Routes A) and B) are unsatisfactory, producing the amino cyclopentene carboxylic acid (IIA) at a relatively high cost since routes A) and B) involve the use of expensive enzyme technology.

We have found a fast, efficient and cost effective resolution process for enantiomeric mixtures of the compound of formula (IIA') and the compound of formula (IIB'), defined below, thus producing the required enantiomer of formula (IIA') at low cost and high yield and, therefore, avoiding the expense of route A) or B).

The process involves the reaction of a chiral base in solution with an enantiomeric mixture of N-protected-cis-4-amino-2-cyclopentene-1-carboxylic acid, the compound of formula (IIA') and the compound of formula (IIB');

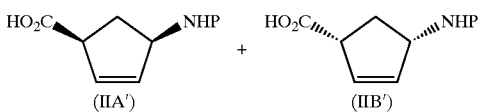

wherein P is a protecting group;
to produce, in a diastereoselective manner by fractional crystallisation the salt of the compound of formula (IIA') as a substantially pure diastereomer.

Thus presented as the first feature of the present invention is a process for the manufacture of an enantiomerically pure compound of formula (IIA')

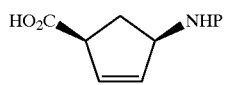

(IIA')

wherein P is a protecting group;
comprising the fractional crystallisation from a suitable solvent of a mixture of the diastereomeric salts of the compound of formula (IIA') and the compound of formula (IIB')

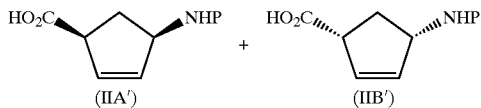

wherein P is a protecting group;
formed with a base of formula (IV)

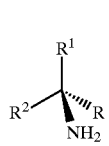

(IV)

wherein R, $R^1$, and $R^2$ are independently selected from H or any hydrocarbyl group provided that each R, $R^1$, and $R^2$ group is different.

Preferably R, $R^1$ and $R^2$ are independently selected from H, $C_{1-6}$ alkyl, $C_{2-6}$ alkenyl, $C_{2-6}$ alkynyl, aryl, $C_{1-6}$ alkylaryl and $C_{3-6}$ cycloalkyl.

Particularly preferred are compounds of formula (IV) wherein R is H, $R^1$ is methyl and $R^2$ is phenyl. The compound of formula (IV) is preferably (R)-(+)-1-phenylethylamine.

By use of the term aryl it is meant either phenyl, optionally substituted phenyl, or naphthyl, preferably phenyl.

Suitable solvents in which to produce and crystallise the diastereomerically pure salts include water; $C_{1-6}$ alkanols such as methanol, ethanol, 2-propanol, 1-propanol and 1-butanol; $C_{3-6}$ alkylmethylketones such as acetone and methyl iso-butyl ketone; cyclic ethers such as dioxane and tetrahydrofuran; mixtures of any of these; aromatic hydrocarbons such as toluene and xylene; $C_{6-8}$ cycloalkanes such as cyclohexane; $C_{6-10}$ alkanes such as n-hexane and n-heptane; and alkyl nitriles such as acetonitrile. Particularly preferred solvents are ethanol and 2-propanol and mixtures of these solvents.

By the term fractional crystallisation it is meant that either the diastereomerically pure salt of the desired compound of formula (IIA') crystallises leaving the diastereomer salt of undesired compound of formula (IIB') in solution or all undesired forms crystallise first leaving the diastereomerically pure salt of the desired compound of formula (IIA') in solution.

By the term substantially pure it is meant that the undesired enantiomer or diastereomer is present to the extent of less than 10% w/w and preferably to the extent of less than 5% w/w.

The salt of the compound of formula (IIA') is readily isolatable by, for example, filtration.

Enantiomerically pure compound of formula (IIA') can be obtained from the diastereomerically pure salt by neutralisation with a mineral acid such as hydrochloric, sulphuric or phosphoric acid.

As a further optional step, the compound of formula (IIA) can be subsequently produced by removing the protecting group of the compound of formula (IIA') with standard methodology such as described in Protective Groups in Organic Synthesis, Green and Wuts, 2nd Ed., 1991 John Wiley & Sons, Inc.

The compound of formula (IIA') may be easily converted to the compound of formula (I') by reduction with reagents capable of converting carboxylic acids to alcohols, for example lithium aluminium hydride or borane, preferably borane. This process step represents a further feature of the invention.

The enantiomeric mixture of compounds of formula (IIA') and (IIB') may be synthesised either:

a) by addition of a protecting group to an enantiomeric mixture of a compound of formula (IIA) and a compound of formula (IIB) by treatment with an appropriate reagent.

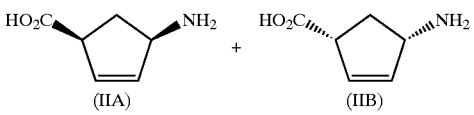

b) from enantiomeric mixtures of the compound of formula (VA') and the compound of formula (VB')

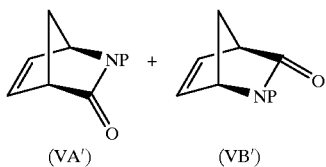

wherein P is a protecting group;
by hydrolysis of the cyclic amide bond.

The enantiomeric mixture of a compound of formula (VA') and a compound of formula (VB') may be synthesised from an enantiomeric mixture of a compound of formula (VA) and a compound of formula (VB) by addition of a protecting group by treatment with an appropriate reagent.

Mixtures of compounds of formula (VA) and (VB), preferably a racemic mixture (the racemic lactam), are commercially available.

Suitable protecting groups include those described in Protective Groups in Organic Synthesis, Green and Wuts, 2nd Ed., 1991 John Wiley & Sons, Inc. as well as methods for their formation and cleavage. Preferred protecting groups are $C_1$–$C_6$ alkyloxycarbonyl, aryloxycarbonyl, $C_2$–$C_{1-6}$ alkenyloxycarbonyl, $C_{1-6}$ alkylaryloxycarbonyl and $C_{3-6}$ cycloalkyloxycarbonyl. By use of the term aryl it is meant either phenyl, optionally substituted phenyl or naphthyl. A particularly preferred protecting group is the tert-butoxycarbonyl (Boc) group.

The addition of the protecting group to mixtures of compounds of formula (VA) and (VB) and subsequent hydrolysis to mixtures of compounds to formula (IIA') and (IIB') occurs in a single "one-pot" reaction without the need to isolate the mixtures of compounds of formula (VA') and (VB') prior to hydrolysis. This represents a further feature of the invention.

The following scheme illustrates the invention using a specific protecting group, tert-butoxycarbonyl, and using (R)-(+)-1-phenylethylamine as the base, and is not intended to limit the scope of the invention.

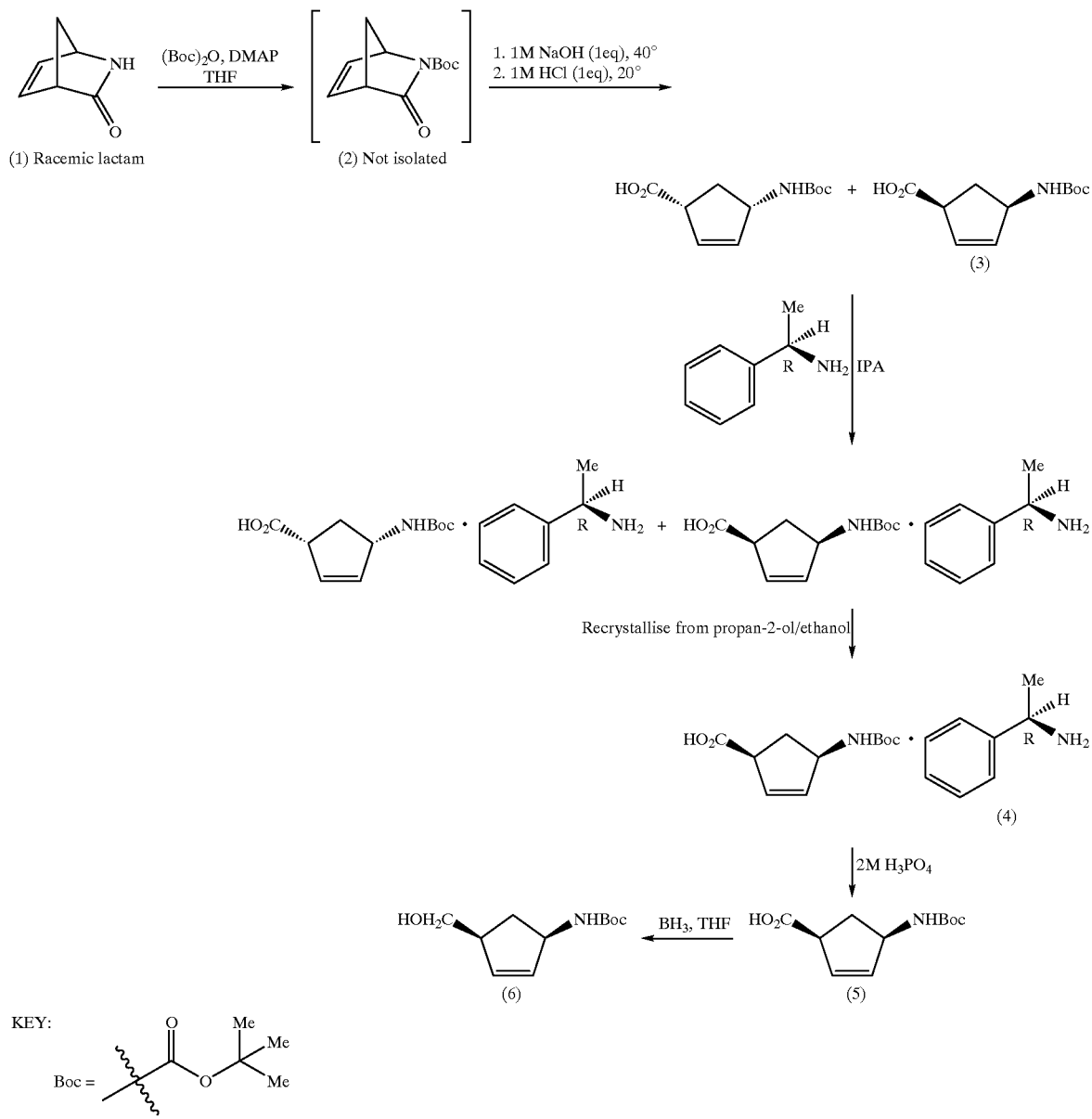

The following examples are intended to illustrate the invention and are not intended to limit the scope of the invention.

As used herein the terms listed have the following meanings:

DMAP is 4-dimethylaminopyridine,

THF is tetrahydrofuran.

EXAMPLES

Example 1

Preparation of Racemic cis-4-[[(1,1-Dimethylethoxy)carbonyl]amino]-2-cyclopentene-1-carboxylic acid (3)

Di-tert-butyl dicarbonate (968 g) was added to a stirred solution of racemic 2-aza bicyclo[2.2.1]hept-5-ene-3-one (1)(440 g) in tetrahydrofuran (THF)(1800 ml). A catalytic amount of 4-dimethylaminopyridine (DMAP)(4.9 g) was added as a single bolus and the solution stirred at ca 25–30° C. until the evolution of carbon dioxide had ceased. A solution of sodium hydroxide (177.4 g) in water (4400 ml) was added to the thus formed 3-oxo-2-azabicyclo[2.2.1]hept-5-ene-2-carboxylic acid, 1,1-dimethylethyl ester (2) and the reaction heated to 40° C. for 15 hours. The reaction mixture was cooled and partitioned with toluene (3500 ml). The phases were separated and the aqueous layer extracted with more toluene (1700 ml). The aqueous layer was treated with activated charcoal (44 g) at ambient temperature, filtered and then acidified to pH3.6 with concentrated hydrochloric acid (400 ml). The precipitated product was filtered off, washed with water (400 ml) then dried in vacuo at 50° C. The yield of 4-[[(1,1-dimethylethoxy)carbonyl]amino]-2-cyclopentene-1-carboxylic acid was 882 g, 96% of theory. Mp 125–28° C.

Example 2

Preparation of (1S-cis)-4-[[(1,1-dimethylethoxy)carbonyl]amino]-2-cyclopentene-1-carboxylic acid, compound with (R)-(+)-1-phenylethylamine (4)

To a hot solution of racemic 4-[[(1,1-dimethylethoxy)carbonyl]amino]-2-cyclopentene-1-carboxylic acid (3) (227.3 g) in propan-2-ol (784 ml) and ethanol (174 ml) was added (R)-(+)-1-phenylethylamine (90.89 g). The solution was cooled to ambient temperature and the resulting solid filtered off, washed with cold propan-2-ol (4×100 ml) and dried in vacuo at 45° C. The yield of (R)-(+)-1-phenylethylamine salt was 126.44 g, 36% of theory. HPLC analysis (Chiracel OD column) indicated a 96.8:3.2 ratio of enantiomeric acids.

The above (R)-(+)-1-phenylethylamine salt was dissolved in a mixture of propan-2-ol (567 ml) and ethanol (126 ml) under reflux. The solution was cooled to approximately 60° C., seeded, and cooled further to ambient temperature. The product was filtered off, washed with cold propan-2-ol (4×100 ml) and dried in vacuo at 45° C. The yield of (R)-(+)-1-phenylethylamine salt (4) was 103.3 g, 85% of theory, Mp 173–4° C. HPLC analysis (Chiracel OD column) indicated a 99.83:0.17 ratio of enantiomeric acids.

Example 3

Preparation of (1S-cis)-4-[[(1,1-dimethylethoxy)carbonyl]amino]-2-cyclopentene-1-carboxylic acid (5)

To a suspension of (1S-cis)-4-[[(1,1-dimethylethoxy)carbonyl]amino]-2-cyclopentene-1-carboxylic acid (4), compound with (R)-(+)-1-phenylethylamine (34.84 g) in toluene (100 ml) and water (100 ml) was added dropwise, over 5 min, phosphoric acid (11.53 g). Ethyl acetate (200 ml) was added and a clear biphasic mixture obtained. The phases were separated and the organic layer concentrated in vacuo at approximately 50° C. to about one quarter of the original volume. The solution was cooled to ambient temperature and the resulting solid filtered off, washed with toluene (50 ml) followed by 2,2,4-trimethylpentane (50 ml) then dried in vacuo at 35° C. The yield of (1S-cis)-4-[[(1,1-dimethylethoxy)carbonyl]amino]-2-cyclopentene-1-carboxylic acid was 21.01 g, 92% of theory, Mp=153–5° C.

Example 4

Preparation of (1R-cis)-[4-(hydroxymethyl)-2-cyclopentene-1-yl]carbamic acid, 1,1-dimethylethyl ester (6)

To a solution of (1S-cis)-4-[[(1,1-dimethylethoxy)carbonyl]amino]-2-cyclopentene-1-carboxylic acid (113.5 g) in tetrahydrofuran (800 ml) at −15° C. under nitrogen was added dropwise over 1 hour a solution of borane/tetrahydrofuran complex in tetrahydrofuran (500 ml of 1.0 M solution). The reaction was stirred for 3 hours whereupon a solution of sodium hydroxide (40 g) in water (400 ml) was added at −15° C., the mixture allowed to attain ambient temperature and stirring continued for a further 2 hours. Water (200 ml) and toluene (500 ml) were added and the biphasic mixture separated. The organic phase was washed with 1N hydrochloric acid (200 ml) followed by water (200 ml) then concentrated in vacua. The resulting oil was crystallised from a mixture of toluene (110 ml) and hexane (180 ml). The product was collected by filtration, washed with a mixture of toluene and hexane (1:1, 50 ml) and dried in vacuo at 35° C. The yield of (1R-cis)-[4-(hydroxymethyl)-2-cyclopentene-1-yl]carbamic acid, 1,1-dimethylethyl ester was 54.0 g, 51% of theory. Mp=68–70° C.

A further 22.0 g of product was recovered from the crystallisation liquors.

What is claimed is:

1. A process for the manufacture of an enantiomerically pure compound of formula (IIA')

wherein P is selected from $C_{1-6}$ alkyloxycarbonyl, aryloxycarbonyl, $C_{2-6}$ alkenyloxycarbonyl, $C_{1-6}$ alkylaryloxycarbonyl and $C_{3-6}$ cycloalkyloxycarbonyl; comprising the fractional crystallisation from a suitable solvent of a mixture of diastereomeric salts of the compound of formula (IIA') and the compound of formula (IIB')

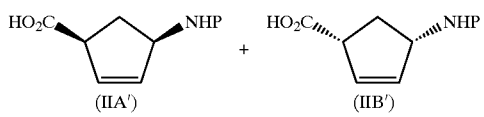

wherein P is as defined above; with a base of formula (IV)

wherein R, $R^1$ and $R^2$ are independently selected from H, $C_{1-6}$ alkyl, $C_{2-6}$ alkenyl, $C_{2-6}$ alkynyl, aryl, $C_{1-6}$ alkylaryl and $C_{3-6}$ cycloalkyl provided that the groups R, $R^1$ and $R^2$ are each different.

2. A process for the manufacture of an enantiomeric mixture of a compound of formula (IIA') and a compound of formula (IIB')

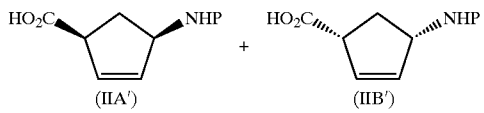

wherein P is selected from $C_{1-6}$ alkyloxycarbonyl, aryloxycarbonyl, $C_{2-6}$ alkenyloxycarbonyl, $C_{1-6}$ alkylaryloxycarbonyl and $C_{3-6}$ cycloalkyloxycarbonyl; comprising the acid or base hydrolysis of an enantiomeric mixture of a compound of formula (VA') and a compound of formula (VB')

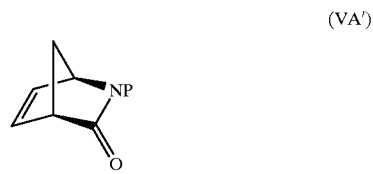

-continued

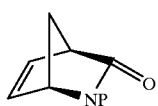
(VB')

wherein P is as defined above.

3. A process for the manufacture of an enantiomeric mixture of a compound of formula (IIA') and a compound of formula (IIB')

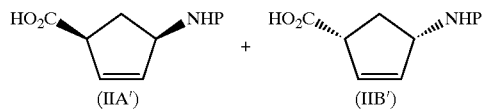

wherein P is selected from $C_{1-6}$ alkyloxycarbonyl, aryloxycarbonyl, $C_{2-6}$ alkenyloxycarbonyl, $C_{1-6}$ alkylaryloxycarbonyl and $C_{3-6}$ cycloalkyloxycarbonyl; comprising the addition of a protecting group to an enantiomeric mixture of a compound of formula (VA) and a compound of formula (VB)

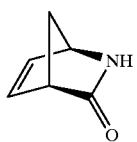
(VA)

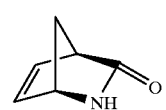
(VB)

by treatment with an appropriate reagent, and the subsequent acid or base hydrolysis of the product in a single 'one-pot' reaction.

4. A process as claimed claim 1 wherein the compound of formula (IV) is (R)-(+)-1-phenylethylamine.

5. A process as claimed in claim 1 wherein the protecting group P is tert-butoxycarbonyl.

* * * * *

UNITED STATES PATENT AND TRADEMARK OFFICE
CERTIFICATE OF CORRECTION

PATENT NO. : 6,147,254
DATED : November 14, 2000
INVENTOR(S) : Sickles et al.

Page 1 of 1

It is certified that error appears in the above-identified patent and that said Letters Patent is hereby corrected as shown below:

Column 3,
Line 48, "alkyl nitrites" should read -- alkyl nitriles --

Column 4,
Line 52, "$C_2$-$C_{1-6}$alkenyloxycarbonyl" should read -- $C_2$-$C_6$alkenyloxycarbonyl --

Column 9,
Line 20, "aryloxyecarbonyl" should read -- aryloxycarbonyl --

Signed and Sealed this

Fourth Day of December, 2001

Attest:

NICHOLAS P. GODICI
Attesting Officer
Acting Director of the United States Patent and Trademark Office